(12) United States Patent
Lee et al.

(10) Patent No.: US 7,247,595 B2
(45) Date of Patent: Jul. 24, 2007

(54) SUPPORTED METALLOCENE CATALYST AND OLEFIN POLYMERIZATION USING THE SAME

(75) Inventors: Bun-Yeoul Lee, Taejeon (KR); Jae-Seung Oh, Taejeon (KR); Joo-Eun Lee, Taejeon (KR); Do-Hoon Lee, Yeosoo (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/289,623

(22) Filed: Nov. 30, 2005

(65) Prior Publication Data

US 2006/0135351 A1    Jun. 22, 2006

Related U.S. Application Data

(63) Continuation-in-part of application No. 10/666,618, filed on Sep. 18, 2003, now Pat. No. 7,041,618, which is a continuation-in-part of application No. 09/526,035, filed on Mar. 15, 2000, now abandoned.

(30) Foreign Application Priority Data

Jun. 22, 1999   (KR) ................ 10-1999-0023575

(51) Int. Cl.
  *B01J 31/00*  (2006.01)
  *C07F 17/00*  (2006.01)
(52) U.S. Cl. .............. 502/103; 502/117; 502/152; 556/11; 556/12; 556/15; 556/16; 556/22; 556/52; 556/53
(58) Field of Classification Search ............ 556/12, 556/22, 52, 53, 11, 15, 16; 502/103, 117, 502/152
See application file for complete search history.

(56) References Cited

U.S. PATENT DOCUMENTS

| | | | |
|---|---|---|---|
| 5,006,500 A | | 4/1991 | Chang |
| 5,240,894 A | | 8/1993 | Burkhardt et al. |
| 5,324,800 A | | 6/1994 | Welborn, Jr. et al. |
| 5,466,766 A | | 11/1995 | Patsidis et al. |
| 5,739,225 A | | 4/1998 | Tazaki et al. |
| 5,767,209 A | * | 6/1998 | McNally ............ 526/160 |
| 5,767,300 A | | 6/1998 | Aulbach et al. |
| 5,814,574 A | * | 9/1998 | McNally ............ 502/103 |
| 5,910,566 A | | 6/1999 | Ko et al. |
| 6,117,811 A | | 9/2000 | Gruter et al. |
| 6,469,113 B1 | * | 10/2002 | Lee et al. ............ 526/126 |
| 2003/0144135 A1 | * | 7/2003 | Llinas et al. ............ 502/103 |

FOREIGN PATENT DOCUMENTS

| | | | |
|---|---|---|---|
| EP | 000293815 | * | 6/1988 |
| EP | 0 293 815 A1 | | 12/1988 |
| EP | 000839836 | * | 5/1998 |
| EP | 0 839 836 A1 | | 6/1998 |
| KR | 98-25282 | * | 7/1998 |
| WO | WO 02/094841 | * | 11/2002 |

OTHER PUBLICATIONS

Lee et al., J. Organomet. Chem., vol. 552 (1998) pp. 313-317.*
Alexaleis, et al., Tetrahedron Lett., 2951 (1988).
Andresen, et al., Angew. Int. Ed. Engl. 15, 630 (1976).
Barklay, et al., Chemistry and Industry (London), 1710 (1964).
Blümel, J. Am. Chem. Soc., 117, 2112 (1995).
Bongini, et al., A Simple and Practical Method for Tetrahydropyranylation of Alcohols and Phenols, Synthesis, 618 (1979).
Dubois, et al., J. Am. Chem. Soc. 115, 1190 (1993).
Kaminsky, Makromol. Chem., Rapid Commun., 14, 239 (1993).
Lee, et al., J. Organomet. Chem., 552, 313 (1998).
Soga, Makromol. Chem., Rapid Commun., 13, 221 (1992).
Soga, Makromol. Chem., Rapid Commun., 15, 139 (1994).

* cited by examiner

*Primary Examiner*—Anthony J. Green
(74) *Attorney, Agent, or Firm*—McKenna Long & Aldridge LLP

(57) ABSTRACT

A metallocene compound represented by the following Chemical Formula 1:

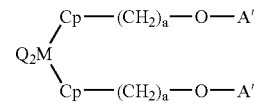

wherein M is a transition metal of Group 4;
Cp denotes a cyclopentadienyl ring unsubstituted or substituted by hydrogen, alkyl, cycloalkyl, aryl, alkenyl, alkylaryl, arylalkyl or arylalkenyl radicals;
Qs, which are the same or different, are halogen radicals, alkyl, alkenyl, aryl, alkylaryl, or arylakyl radicals having 1 to 20 carbon atoms, or alkylidene radicals having 1 to 20 carbon atoms;
A' is methoxymethyl, t-butoxymethyl, tetrahydropyranyl, tetrahydrofuranyl, 1-ethoxyethyl, 1-methyl-1-methoxyethyl, or t-butyl; and
a is an integer of 4 to 8.
  The metallocene compounds in this invention can be strongly supported on the inorganic support, and the supported catalyst of this invention allows for an olefin polymerization process without any fouling in the reactor, and produces a polymer with better morphology and bulk density.

7 Claims, 2 Drawing Sheets

SUPPORTED METALLOCENE CATALYST AND OLEFIN POLYMERIZATION USING THE SAME

This application is continuation in part application of U.S. application Ser. No. 10/666,618 filed Sep. 18, 2003 now U.S. Pat. No. 7,041,618, which is a continuation in part application of U.S. application Ser. No. 09/526,035 filed Mar. 15, 2000 now abandoned, which claimed priority to Korean Patent Application No. 10-1999-0023575 filed Jun. 22, 1999, each of which are incorporated by reference for all purposed as if fully set forth herein.

BACKGROUND OF THE INVENTION (a) Field of the Invention

The present invention relates to a metallocene compound having a functional group that facilitates the preparation of a supported metallocene catalyst for olefin polymerization and the olefin polymerization using the same.

(b) Description of the Related Art

In 1976, Professor Kaminsky of Germany reported that olefin polymerization could be accomplished using zirconocene dichloride compound as a catalyst with a methylaluminoxane (MAO) as a co-catalyst which was obtained through partial hydrolysis of trimethylaluminum (A. Anderson, J. G. Corde. J. Herwing; W. Kaminsky, A. Merck, R. Mottweiler, J. Pein, H. Sinn, and H. J. Vollmer, Angew. Chem, Int. Ed. Engl. 15, 630 (1976)).

Thereafter, Exxon showed that the activity of a catalyst and the molecular weight of the produced polymer could be controlled by changing the substituents on the cyclopentadienyl ligand, and issued a patent (U.S. Pat. No. 5,324,800) on olefin polymerization utilizing the filed metallocene compounds with various substituent groups. A homogeneous metallocene catalyst shows unique polymerization characteristics which can not be obtained by conventional Ziegler-Natta catalysts. That is, molecular weight distribution of the produced polymer is narrow, co-polymerization is easy, and the co-monomer distribution is uniform. In the case of propylene polymerization, the tacticity of polymer can be controlled according to the molecular symmetry of catalyst. These unique characteristics not only opened up a way to produce new polymers which are not attainable by the conventional Ziegler-Natta catalyst, but also provided a way to make the tailor-made polymers. Accordingly, there has been continuous interest on this catalyst system.

In a gas phase or a slurry process, particle morphology and bulk density of produced polymer should be controlled to increase the mobility of polymer and the production rate per reactor unit volume. Also, the reactor fouling, a phenomenon that polymer sticks to reactor wall and agitator blades, should be avoided for a continuous operation. To solve these problems the catalyst should be anchored on a suitable support.

Described below are conventional preparation methods for supported metallocene catalysts.

(1) a metallocene compound is adsorbed on a support, and then activated by treatment with aluminoxane (W. Kaminsky, Makromol. Chem., Rapid Commun. 14, 239 (1993));

(2) aluminoxane is supported first, and then a metallocene compound is supported (K. Soga, Makromol. Chem. Rapid Commun. 13, 221 (1992); U.S. Pat. Nos. 5,006,500; 5,086,025);

(3) a metallocene compound is treated with aluminoxane, and then adsorbed on a support (U.S. Pat. No. 5,240,894); and (4) the anchoring of catalyst is achieved by a chemical reaction between the ligand of a metallocene compound and a support.

In one case, metal is ligated after ligand is supported. (K. Soga, H. J. Kim, T. Shiono, Makromol., Rapid Commun. 15, 139 (1994), Japanese Laid-open Patent No. Heisei 6-56928, U.S. Pat. No. 5,466,766). In the other case, a metallocene compound with suitable ligands is prepared and then it is supported onto a support by chemical reaction. The suitable ligands in this case usually contain silicon based functional groups such as alkoxysilane or halosilane (European Patent No. 293815, U.S. Pat. No. 5,767,300, European Laid-open Patent No. 839836, Korean Patent application No. 98-12660, and 99-06955). However, the metallocene compounds with silicon containing functional group are not easy to make and do not have good stabilities. For example, European Laid-open Patent No. 839836 discloses a metallocene compound having a functional group of —OSiMe$_3$. The yield in the metallation step, which is the last step in synthesis, is only around 28~51% which is a disadvantage in commercial application.

U.S. Pat. No. 5,814,574 discloses the supported polymerization catalyst which is prepared by the binding of inorganic support with metallocene compound containing a functional group selected from alkoxyalkyl, heterocycle oxygen radical, or alkyl heterocycle oxygen radical. U.S. Pat. No. 5,767,209 discloses a polymerization of olefins under a suitable temperature and pressure utilizing a supported catalyst. In this patent, the metallocene compound with Lewis base functionalities such as oxygen, silicon, phosphorus, nitrogen or sulfur atoms is bound to an inorganic support in the absence of aluminoxane to give a supported catalyst. However, the catalyst bound to and supported on an inorganic support surface by the Lewis acid-base reaction leaches out of the surface upon activation with Lewis acidic aluminoxane co-catalyst. The leaching of the catalyst will result in reactor fouling and irregular morphology which are detrimental in a slurry or a gas phase process.

Metallocene catalyst with a suitable functional group can be supported onto a silica surface by the reaction of alkoxysilane or halosilane functional group with surface hydroxyl group or highly reactive siloxane group, which is formed from the dehydroxylation of the silica above 600° C., as shown in Reaction Formula 1~3.

[Reaction Formula 1]

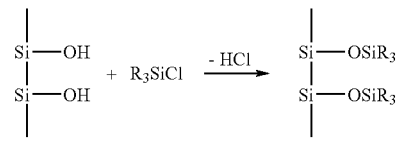

[Reaction Formula 2]

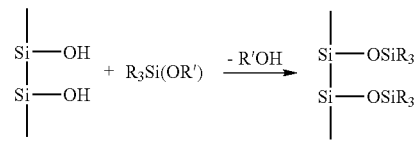

-continued

[Reaction Formula 3]

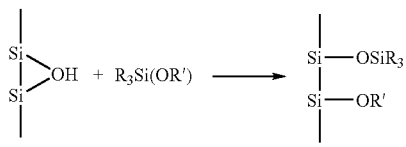

EP 293815 A1 discloses a method in which a supported metallocene catalyst is prepared by the reaction of a metallocene compound containing —C—SiR$_2$(OR') functional group (wherein R is a C1-4 alkyl, C6-10 aryl, or C1-4 alkoxy, and OR' is a C1-4 alkoxy) with a support hydroxyl group on its surface (See the Reaction Formula 4).

[Reaction Formula 4]

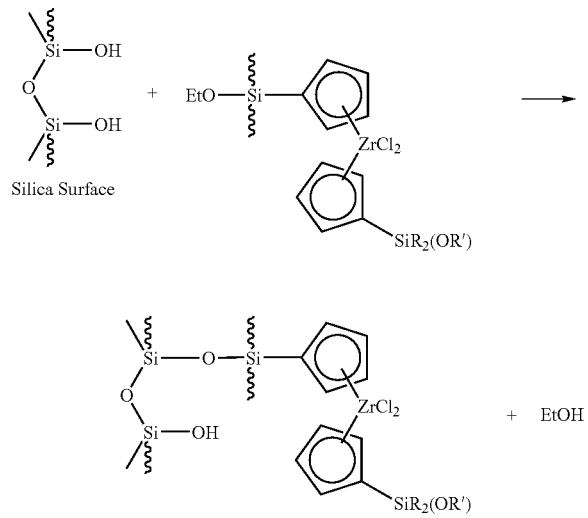

Silica Surface

Herein, an Si—OR' (silicon-based groups) bond of the metallocene compound is reacted with an Si—OH group of the support material to produce a strongly bound-supported metallocene catalyst via Si—O—Si bond formation. However, alkyl alcohol (R'OH) by-product is also formed during the reaction, which is possibly acted as a catalyst poison to lower activity of the final catalyst.

Especially, the Reaction Formula 3 is reported recently (*J. Am. Chem. Soc.* 117, 2112, (1995); *J. Am. Chem. Soc.* 115, 1190, (1993)) and is advantageous to the preparation of supported metallocene catalyst because side reactions are minimized (Korean Patent application No 98-12660). As mentioned above, however, the catalyst with siloxane functional group is not easy to make and has low stability. For example, the catalysts containing an alkoxysilane group, [HMe$_2$Si—O—(CH$_2$)$_6$—C$_5$H$_4$]$_2$ZrCl$_2$ and [Me$_3$Si—O—(CH$_2$)$_6$—C$_5$H$_4$]$_2$ZrCl$_2$], were disclosed in the examples and comparative examples of Korean Patent Application No 99-06955 which was applied by the present inventors. In the examples, the yield in the zirconation step which is the last step of the synthesis, was below 60% and the catalysts was observed to degrade slowly over an extended period under an inert gas atmosphere at room temperature.

SUMMARY OF THE INVENTION

It is an object of the present invention to provide a metallocene compound having a functional group that facilitates the preparation of the supported metallocene catalyst for olefin polymerization.

It is another object of the present invention to provide a supported metallocene catalyst using the above metallocene compound.

It is still another object of the present invention to provide a method for preparing a supported metallocene catalyst using the above metallocene compound.

It is still another object of the present invention to provide a process for preparing olefin polymer using the supported metallocene catalyst.

In order to achieve the above objects, the present invention provides a metallocene compound, represented by the following Chemical Formula 1:

[Chemical Formula 1]

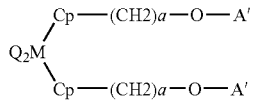

Wherein, M is a transition metal of Group 4'
Cp denotes a cyclopentadienyl ring unsubstituted or substituted by hydrogen, alkyl, cycloalkyl, aryl, alkenyl, alkylaryl, arylalkyl or arylalkenyl ardical;
Q, which can be the same or different, is a halogen radical, an alkyl, alkenyl, aryl, alkylaryl, or arylakyl radical having 1 to 20 carbon atoms, or an alkylidene radical having 1 to 20 carbon atoms;
A' is methoxymethyl, t-butoxymethyl, tetrahydropyranyl, tetahydrofuranyl, 1-ethoxylethyl, 1-methyl-1-methoxyethyl, or t-butyl; and
a is an integer of 4 to 8.

The present invention also provides a supported metallocene catalyst represented by the following Chemical Formula 2:

[Chemical Formula 2]

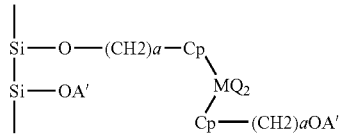

Wherein, M is a transition metal of Group 4'
Cp denotes a cyclopentadienyl ring unsubstituted or substituted by hydrogen, alkyl, cycloalkyl, aryl, alkenyl, alkylaryl, arylalkyl or arylalkenyl ardical;
Q, which can be the same or different, is a halogen radical, an alkyl, alkenyl, aryl, alkylaryl, or arylakyl radical having 1 to 20 carbon atoms, or an alkylidene radical having 1 to 20 carbon atoms;
A' is methoxymethyl, t-butoxymethyl, tetrahydropyranyl, tetahydrofuranyl, 1-ethoxylethyl, 1-methyl-1-methoxyethyl, or t-butyl; and
a is an integer of 4 to 8.

The present invention also provides a method for preparing a supported metallocene catalyst represented by the following Cheical Formula 2, which method comprises the step of reacting a metallocene compound of the following Chemical Formula 1 with a silica support of the following Chemical Formula 3 in an organic solvent:

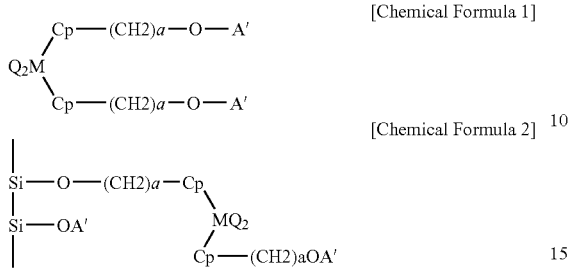
[Chemical Formula 1]

[Chemical Formula 2]

Wherein, M is a transition metal of Group 4'
Cp denotes a cyclopentadienyl ring unsubstituted or substituted by hydrogen, alkyl, cycloalkyl, aryl, alkenyl, alkylaryl, arylalkyl or arylalkenyl ardical;
Q, which can be the same or different, is a halogen radical, an alkyl, alkenyl, aryl, alkylaryl, or arylakyl radical having 1 to 20 carbon atoms, or an alkylidene radical having 1 to 20 carbon atoms;
A' is methoxymethyl, t-butoxymethyl, tetrahydropyranyl, tetahydrofuranyl, 1-ethoxyethyl, 1-methyl-1-methoxyethyl, or t-butyl; and
a is an integer of 4 to 8.

[Chemical Formula 3]

whereby one of O-A' bond in the Chemical Formula 1 is cleaved so that the metallocene compound is bonded to a silica atom of the silica support via oxygen atom, and simultaneously A' is bonded to another silica atom of the silica support via oxygen atom (See the Reaction Formula 5).

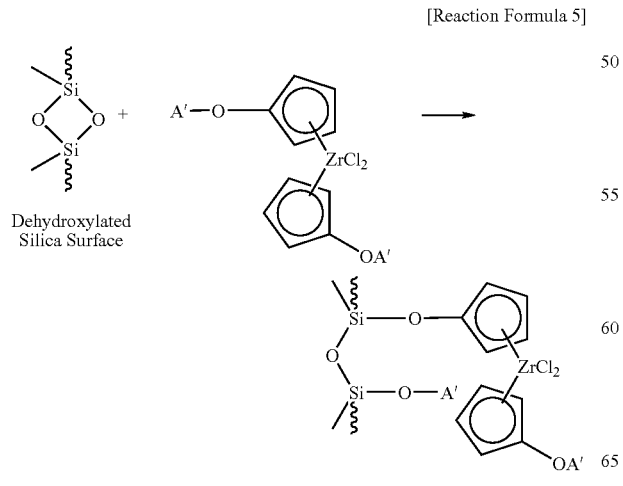
[Reaction Formula 5]

Dehydroxylated Silica Surface

The present invention also provides a process for olefin polymerization which comprises conducting the polymerization in the presence of the catalyst system comprising:
a) a supported metallocene catalyst represented by the above Chemical Formula 2; and
b) a co-catalyst(s) selected from the compounds described by Chemical Formula 4, 5 or 6 shown below:

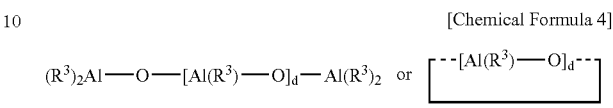
[Chemical Formula 4]

(wherein each $R^3$, which can be the same as or different from other $R^3$, is a halogen radical, a hydrocarbyl radical having from 1 to 40 carbon atoms, or a halogen substituted hydrocarbyl radical having from 1 to 40 carbon atoms; and d is an integral number greater than 2);

$Al(R^4)_3$      [Chemical Formula 5]

(wherein each $R^4$, which can be the same as or different from other $R^4$, is a halogen radical, a hydrocarbyl radical having from 1 to 40 carbon atoms, or a halogen substituted hydrocarbyl radical having from 1 to 40 carbon atoms);

$[L]^+[NE_4]^-$      [Chemical Formula 6]

(wherein, $[L]^+$ is a cation composed of an inorganic or organic group;
N is an element of Group 13 (III B in the previous IUPAC form); and
each E, which can be the same as or different from other E, is an aryl radical having from 6 to 40 carbon atoms, where at least one of the hydrogen radicals of the aryl group is substituted with a halogen radical, a hydrocarbyl radical having from 1 to 40 carbon atoms, an alkoxy radical, a phenoxy radical, or a hydrocarbyl radical having from 1 to 40 carbon atoms with nitrogen, phosphorus, sulfur, or oxygen atom).

The present invention also provides a metallocene compound represented by the following Chemical Formula 7 or 8 in which at least one of the hydrogen radical of R1, R2 or B is substituted by a radical selected from the groups consisting of the compounds represented by the following Chemical Formula 12:

$(C_5R^1_m)_pB_s(C_5R^1_m)MQ_{3-p}$      [Chemical Formula 7]

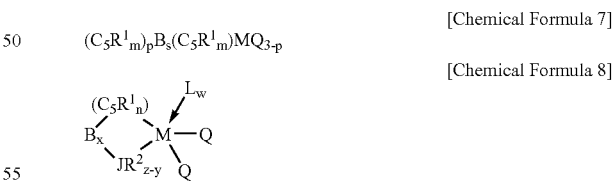
[Chemical Formula 8]

(wherein M is a transition metal of Group 4 (IVA in the previous IUPAC form);
$(C_5R^1_m)$ and $(C_5R^1_n)$ are a cyclopentadienyl, a substituted cyclopentadienyl ligand, or a substituted cyclopentadienyl ligand in which two adjacent carbon atoms of a $C_5$ are joined together to form one or more $C_4$-$C_{16}$ rings by a hydrocarbyl radical, in which each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, or a metalloid of Group 14 (IVB in the previous IUPAC form) substituted by hydrocarbyl radical;

B is an alkylene carbon chain, arylene carbon chain, alkenylene carbon chain, dialkyl germanium, dialkyl silicon, alkyl phospine, or alkyl amine radical substituting on and bridging two cyclopentadienyl ligands, or a cyclopentadienyl ligand and $JR^2_{z-y}$ ligands by a covalent bond;

$R^2$ is a hydrogen radical, or an alkyl, aryl, alkenyl, alkylaryl, or arylalkyl radical having from 1 to 40 carbon atoms;

J is an element of Group 15 (VB in the previous IUPAC form) or Group 16 (VIB in the previous IUPAC form);

each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1 and p is 0, 1 or 2;

provided that when p is 0, then s is 0; when s is 1, then m is 4; and when s is 0, then m is 5;

z is a valence number of J;

provided that when J is an atom of Group 15 (VB in the previous IUPAC form), then z is 3; and when J is an atom of Group 16 (VIB in the previous IUPAC form), then z is 2;

x is 0 or 1;

provided that when x is 0, then n is 5, y is 1, and w is greater than 0; when x is 1, then n is 4, y is 2, and w is 0);

[Chemical Formula 12]

Wherein, Z is oxygen atom or sulfur atom;

each R', which can be the same or different, is a hydrogen radical, an alkyl, cycloalkyl, aryl, alkenyl, alkylaryl, arylalkyl, or arylalkenyl radical having from 1 to 20 carbon atoms and two R' can join together to form a ring;

Y is a hydrogen radical, an alkyl, cycloalkyl, aryl, alkenyl, alkylaryl, arylalkyl, or arylalkenyl radical, alkoxy, aryloxy, alkylthio, arylthio having from 1 to 20 carbon atoms, a phenyl, or a substituted phenyl, and Y and R' can join together to form a ring; and a is an integer of 4 to 8, provided that when Z is sulfur atom, then Y is alkoxy or aryloxy, and when Y is not alkoxy or aryloxy, Z is an oxygen atom.

The present invention also provides a supported metallocene catalyst prepared by the reaction of a) the above metallocene compound represented by the Chemical Formula 7 or 8 in which at least one of the hydrogen radical of R1, R2 or B is substituted by a radical selected from the groups consisting of the compounds represented by the Chemical Formula 12: and b) a silica supported represented by the above Chemical Formula 3.

The present invention also provides a method for preparing a supported metallocene compound, which method comprises the step of reacting the above metallocene compound represented by the Chemical Formula 7 or 8 in which at least one of the hydrogen radical of R1, R2 or B is substituted by a radical selected from the groups consisting of the compounds represented by the Chemical Formula 12 with a silica support represented by the Chemical Formula 3 in an organic solvent.

The present invention also provides a process for olefin polymerization which comprises conducting the polymerization in the presence of the catalyst system comprising:

a) a supported metallocene catalyst prepared by the reaction of:

i) the above metallocene compound represented by the Chemical Formula 7 or 8 in which at least one of the hydrogen radical of R1, R2 or B is substituted by a radical selected from the groups consisting of the compounds represented by the Chemical Formula 12: and ii) a silica supported represented by the above Chemical Formula 3; and b) a co-catalyst(s) selected from the compounds described by the above Chemical Formula 4, 5 or 6.

BRIEF DESCRIPTION OF THE DRAWINGS

Further objects and other advantages of the present invention will become apparent from the following description in conjunction with the attached drawings, in which.

DETAILED DESCRIPTION OF THE PREFERRED EMBODIMENTS

Figure 1:
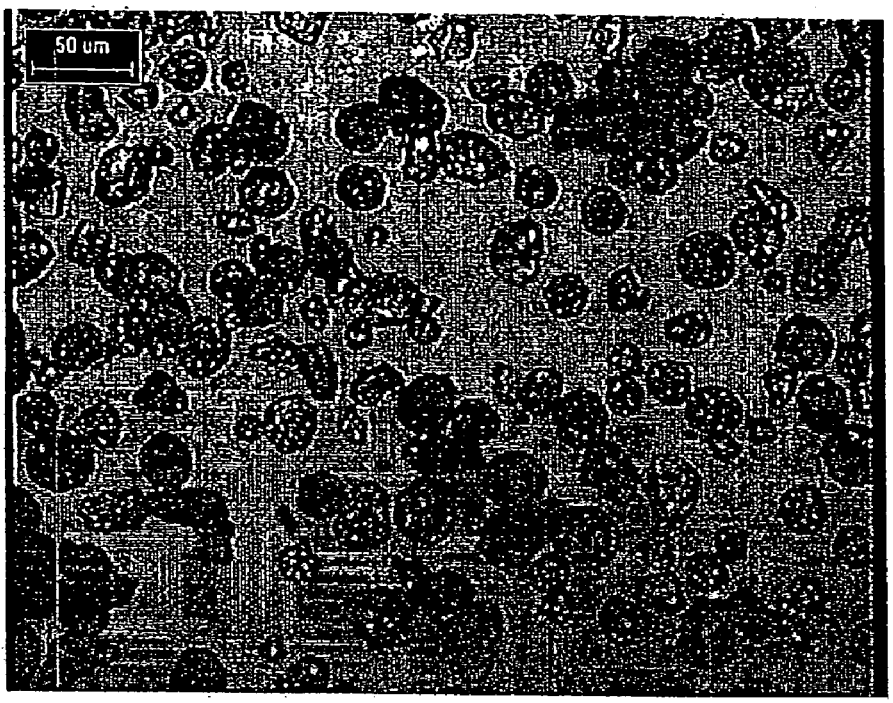
FIG. 1 is an optical microscope photograph of the supported catalyst morphology prepared by supporting catalyst of example 5 onto a slilca surface (100 times magnified)

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, the drawings and descriptions are to be regarded as illustrative in nature, not restrictive.

The present invention is described in detail as follows:

A metallocene compound of the present invention which is useful in the preparation of the supported metallocene catalyst is represented by the following Chemical Formula 7 or 8 in which at least one of the hydrogen radical of $R^1$, $R^2$ or B is substituted by a radical selected from groups represented by the following Chemical Formula 9, 10, or 11:

[Chemical Formula 7]

-continued

[Chemical Formula 8]

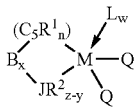

(wherein M is a transition metal of Group 4 (IVA in the previous IUPAC form);
($C_5R^1_m$) and ($C_5R^1_n$) are a cyclopentadienyl, a substituted cyclopentadienyl ligand, or a substituted cyclopentadienyl ligand in which two adjacent carbon atoms of a $C_5$ are joined together to form one or more $C_4$-$C_{16}$ rings by a hydrocarbyl radical, in which each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, or a metalloid of Group 14 (IVB in the previous IUPAC form) substituted by hydrocarbyl radical;
B is an alkylene carbon chain, arylene carbon chain, alkenylene carbon chain, dialkyl germanium, dialkyl silicon, alkyl phospine, or alkyl amine radical substituting on and bridging two cyclopentadienyl ligands, or a cyclopentadienyl ligand and $JR^2_{z-y}$ ligands by a covalent bond;
$R^2$ is a hydrogen radical, or an alkyl, aryl, alkenyl, alkylaryl, or arylalkyl radical having from 1 to 40 carbon atoms;
J is an element of Group 15 (VB in the previous IUPAC form) or Group 16 (VIB in the previous IUPAC form);
each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;
L is a Lewis base;
s is 0 or 1 and p is 0, 1 or 2;
provided that when p is 0, then s is 0; when s is 1, then m is 4; and when s is 0, then m is 5;
z is a valence number of J;
provided that when J is an atom of Group 15 (VB in the previous IUPAC form), then z is 3; and when J is an atom of Group 16 (VIB in the previous IUPAC form), then z is 2;
x is 0 or 1;
provided that when x is 0, then n is 5, y is 1, and w is greater than 0; when x is 1, then n is 4, y is 2, and w is 0);

[Chemical Formula 9]

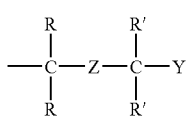

(wherein Z is oxygen atom or sulfur atom;
each R, which can be the same as or different from other R, is a hydrogen radical, an alkyl, cycloalkyl, aryl, alkenyl, alkylaryl, arylalkyl, or arylalkenyl radical having from 1 to 20 carbon atoms;
each R', which can be the same as or different from other R', is hydrogen radical, an alkyl, cycloalkyl, aryl, alkenyl, alkylaryl, arylalkyl, or arylalkenyl radical having from 1 to 20 carbon atoms and two R' can join together to form a ring;
Y is a hydrogen radical, an alkyl, cycloalkyl, aryl, alkenyl, alkylaryl, arylalkyl, or arylalkenyl radical, alkoxy, aryloxy, alkylthio, arylthio having from 1 to 20 carbon atoms, a phenyl, or a substituted phenyl, and Y and R' can join together to form a ring;
provided that when Z is sulfur atom, then Y is alkoxy or aryloxy);

[Chemical Formula 10]

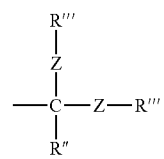

(wherein Z is an oxygen atom or a sulfur atom and at least one Z is an oxygen atom;
R" is a hydrogen radical, an alkyl, cycloalkyl, aryl, alkenyl, alkylaryl, arylalkyl, or arlalkenyl radical having from 1 to 40 carbon atoms, and R" and R'" can join together to form a ring;
each R'", which can be the same as or different from other R'", is a hydrogen radical, an alkyl, cycloalkyl, aryl, alkenyl, alkylaryl, arylalkyl, or arylalkenyl radical having from 1 to 40 carbon atoms and two R'" can join together to form a ring);

[Chemical Formula 11]

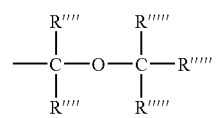

(wherein each R"", which can be the same as or different from other R"", is a hydrogen radical, an alkyl, cycloalkyl, aryl, alkenyl, alkylaryl, arylalkyl, or arylalkenyl radical having from 1 to 40 carbon atoms;
each R'"", which can be the same as or different from other R'"", is a hydrogen radical, an alkyl, cycloalkyl, aryl, alkenyl, alkylaryl, arylalkyl, or arylalkenyl radical having from 1 to 40 carbon atoms and two neighboring R'"" can join together to form a ring;
provided that when at least one of the R"" is hydrogen radical, then none of the R'"" is a hydrogen radical; and when at least one of the R'"" is hydrogen radical, then none of the R"" is a hydrogen radical).

Preferably, in the above Chemical Formula 7 or 8, at least one of the hydrogen radical of R1, R2 or B is substituted by a radical selected from the groups consisting of the compounds represented by the following Chemical Formula 12:

[Chemical Formula 12]

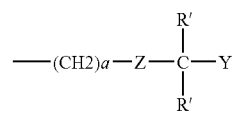

Wherein, Z is oxygen atom or sulfur atom;
each R', which can be the same or different, is a hydrogen radical, an alkyl, cycloalkyl, aryl, alkenyl, alkylaryl, arylalkyl, or arylalkenyl radical having from 1 to 20 carbon atoms and two R' can join together to form a ring;

Y is a hydrogen radical, an alkyl, cycloalkyl, aryl, alkenyl, alkylaryl, arylalkyl, or arylalkenyl radical, alkoxy, aryloxy, alkylthio, arylthio having from 1 to 20 carbon atoms, a phenyl, or a substituted phenyl, and Y and R' can join together to form a ring; and a is an integer of 4 to 8, provided that when Z is sulfur atom, then Y is alkoxy or aryloxy, and when Y is not alkoxy or aryloxy, Z is an oxygen atom.

More preferably, in the above Chemical Formula 12, Y is a hydrogen radical, an alkyl, cycloalkyl, aryl, alkenyl, alkylaryl, arylalkyl, or arylalkenyl radical having from 1 to 20 carbon atoms, or a phenyl substituted or unsubstituted.

Most preferably, in the above Chemical Formula 12, —CR'$_2$Y is t-butyl.

When —CR'$_2$Y consists of only carbon and hydrogen atoms without a heteroatom such as oxygen, the supported catalyst is the most active for olefin polymerization.

In addition, the metallocene compound of the present invention can be preferably represented by the following Chemical Formula 1:

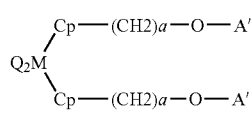

[Chemical Formula 1]

Wherein, M is a transition metal of Group 4'

Cp denotes a cyclopentadienyl ring unsubstituted or substituted by hydrogen, alkyl, cycloalkyl, aryl, alkenyl, alkylaryl, arylalkyl or arylalkenyl ardical;

Q, which can be the same or different, is a halogen radical, an alkyl, alkenyl, aryl, alkylaryl, or arylakyl radical having 1 to 20 carbon atoms, or an alkylidene radical having 1 to 20 carbon atoms;

A' is methoxymethyl, t-butoxymethyl, tetrahydropyranyl, tetahydrofuranyl, 1-ethoxyethyl, 1-methyl-1-methoxyethyl, or t-butyl; and a is an integer of 4 to 8.

Also, the present invention provides a supported metallocene catalyst using the above metallocene compound and an olefin polymerization process using the supported metallocene catalyst.

The metallocene compound in this invention is good for the preparation of supported catalyst due to the presence of suitable ligand functional group such as acetal, ketal, tertiary alkoxyalkyl, benzyloxyakyl, substituted benzyloxyalkyl, monothioacetal or monothioketal. These ligands can be introduced by replacing at least one of the hydrogen radical of R$^1$, R$^2$ or B of the above Chemical Formula 7 or 8 with a radical selected from groups represented by the above Chemical Formula 9, 10, or 11.

Examples of the metallocene compounds are as follows:

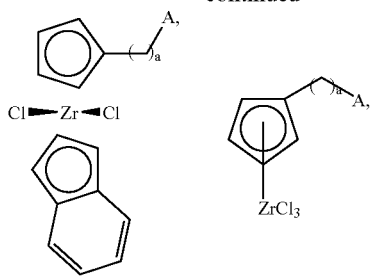

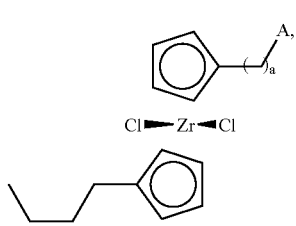

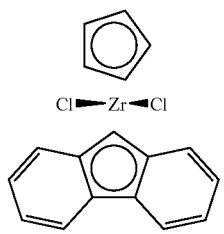

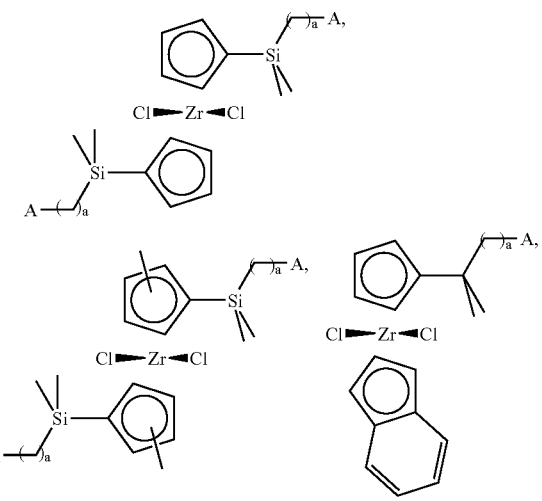

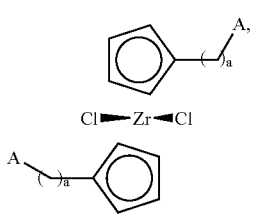 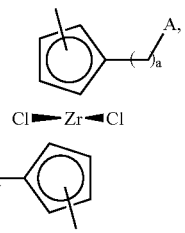 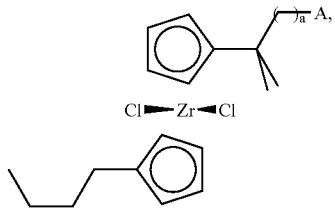

-continued

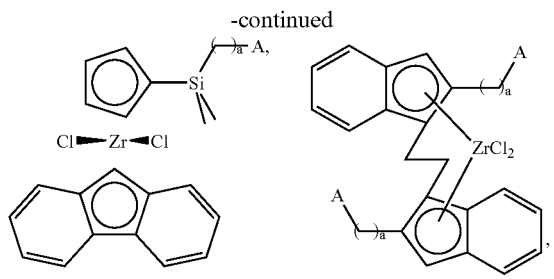

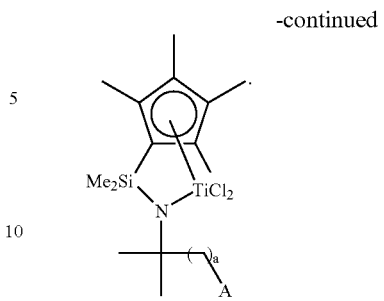

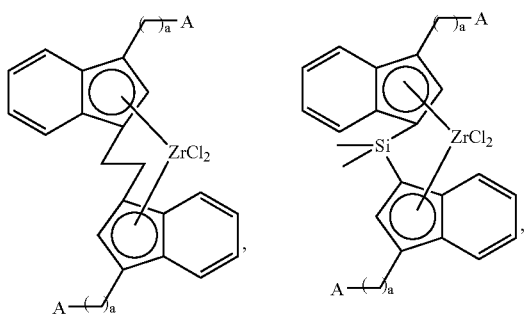

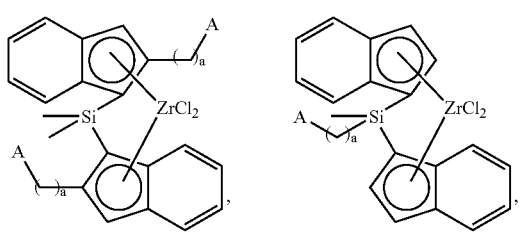

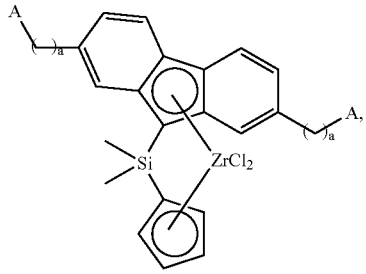

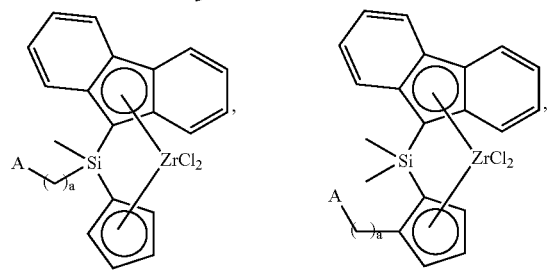

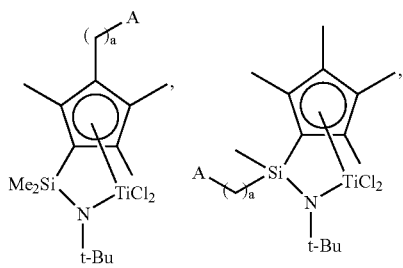

-continued

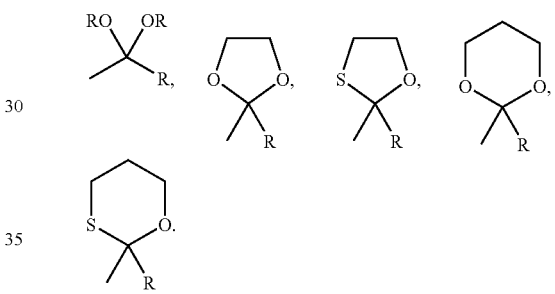

wherein A can be a functional group of OA' (wherein A' is an methoxymethyl, methylthiomethyl, t-butylthiomethyl, benzyloxymethyl, t-butoxymethyl, tetrahydropyranyl, 1-methoxycyclohexyl, tetrahydrofuranyl, 1-ethoxyethyl, 1-methyl-1-methoxyethyl, 1-methyl-1-benzyloxyethyl, t-butyl, diphenylmethyl, or triphenylmethyl), or a functional group having the structure represented by the following examples (wherein R is a hydrocarbyl radical having 1 to 40 carbons):

In the present invention, the substituent A' is preferably methoxymethyl, t-butoxymethyl, tetrahydropyranyl, tetahydrofuranyl, 1-ethoxylethyl, 1-methyl-1-methoxyethyl, or t-butyl, and more preferably t-butyl. When X is t-butyl consisting of only carbon and hydrogen without a heteroatom such as an oxygen, its supported catalyst is the most active for olefin polymerization compared to the others.

In the above exercises a is an integral number from 1 to 40. The distance from the supported metallocene catalyst to the support surface is determined by the value of a. It is possible that the oxygen atom of the siloxane group on the support surface coordinates to the metal center of the catalyst, leading to a decreased activity by converting active species to inactive species. When a is 4 to 8, the increased ring strain of the mid-size cyclic ring prohibits the coordination of the oxygen to the metal center. Therefore, the chance of formation of the inactive species is greatly decreased hence a catalyst shows superior activity when a is 4 to 8. When a is 6, catalyst is the most active hence most preferable. Detailed studies are published by the present inventors previously (J. Organomet. Chem. 552, 313, (1998)).

The metallocene compounds in this invention can be synthesized by a conventional method. That is, a substituted cyclopentadienyl group with a suitable functional group such as acetal, ketal, tertiary alkoxyalkyl, benzyloxyalkyl, substituted benzyloxyalkyl, monothioacetal, or monothioketal is prepared by the corresponding organic reaction and then reacted with a zirconium tetrachloride.

The cyclopentadienyl compound containing functional group such as acetal, ketal, tertiary alkoxyalkyl, benzyloxyalkyl, substituted benzyloxyalkyl, monothioacetal, or monothioketal is prepared by the reaction of NaCp (sodium cyclopentadienide) with a organic compound containing both the halogen atom and the functional group listed above.

The organic compounds containing both the halogen atom and the functional group such as acetal, ketal, tertiary alkoxyalkyl, benzyloxyalkyl, substituted benzyloxyalkyl, monothioacetal, or monothioketal can be synthesized from compounds containing both the halogen atom and another functional groups such as aldehyde, ketone, or alcohol according to the methods described in the "Protective group in organic synthesis" by T. W. Greene and P. G. M. Wuts. However, the synthesis of the compounds is not limited by the method described above. The Reaction Formulas 4~6 shows some examples of the desired reactions:

[Reaction Formula 6]

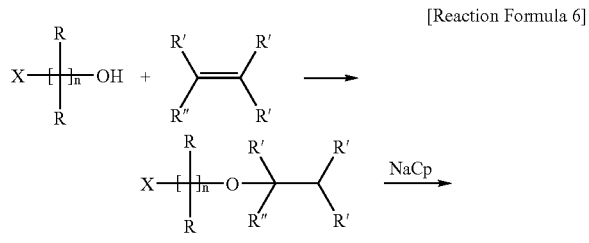

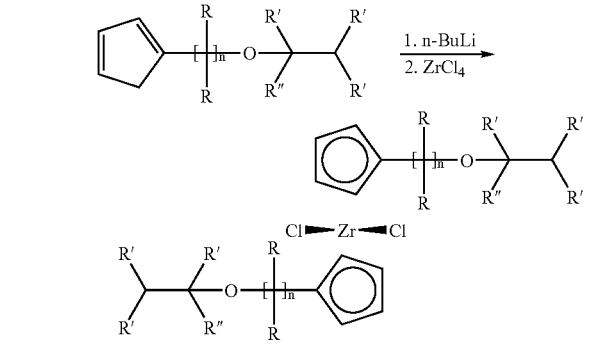

[Reaction Formula 7]

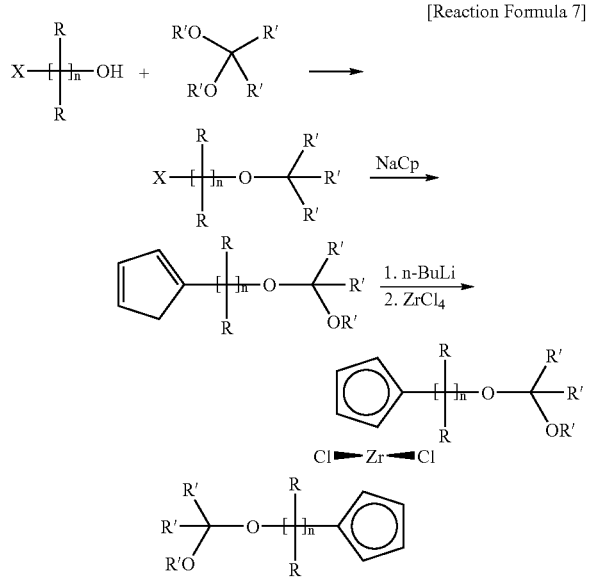

[Reaction Formula 8]

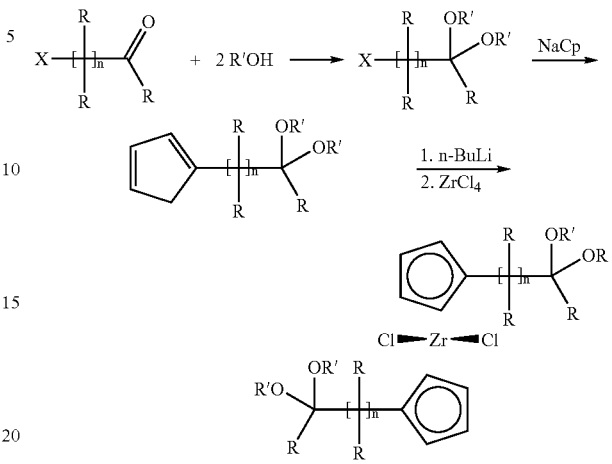

wherein X is halogen; each R and R', which can be same or different, is a hydrogen radical, an alkyl, cycloalkyl, aryl, alkenyl, alkylaryl, arylalkyl, or arylalkenyl radical, and two R' can join together to form a ring; and R" is an alkoxy, aryloxy, alkyl, cycloalkyl, aryl, alkenyl, alkylaryl, arylalkyl, or arylalkenyl radical, and R" can join together to form a ring with R'.

The supported metallocene catalyst of the present invention is prepared by the reaction of the metallocene compound described above with a dehydroxylated silica calcined above 600° C. The silica calcined above 600° C. has a highly reactive siloxane group which can react with a compound containing alkoxysilane group as shown in Reaction Formula 3 (J. Am. Chem. Soc. 117, 2112, (1995); J. Am. Chem. Soc. 115, 1190, (1993)). The silica support used in the preparation of the supported catalyst of the present invention preferably has hydroxyl group amount of less than 0.5 mmol/g silica. The supported catalyst shows superior activity when a silica support has hydroxyl group amount of less than 0.5 mmol/g silica. Furthermore, patents utilizing the reactivity of dehydroxylated silica toward alkoxysilane were already applied (Korean Patent application No. 98-12660, and 99-06955, European Laid-open Patent No. 839836).

However, the reactivity of the dehydroxylated silica containing the highly reactive siloxane group towards acetal, ketal, tertiary alkoxyalkyl, benzyloxyalkyl, substituted benzyloxyalkyl, monothioacetal, or monothioketal is not reported yet. This reaction leads to a new chemical bond by the cleavage of the C—O bond in the above functional groups.

This invention employs the reaction of the dehydroxylated silica containing highly reactive siloxane with acetal, ketal, tertiary alkoxyalkyl, benzyloxyalkyl, substituted benzyloxyalkyl, monothioacetal, or monothioketal which are usually used as a protection group of the alcohol, aldehyde, or ketone in the conventional organic reactions. The C—O bond in the functional group mentioned above can be easily cleaved and the functional groups are transformed back to alcohol, aldehyde or ketone upon the cleavage of the C—O bond, which is the required feature of the protection group.

This invention utilizes the reaction of the highly reactive siloxane group on the silica surface with the above functional group containing the labile C—O bond as shown in Reaction Formulae 9a and 9b.

benzyloxy alkyl, substituted benzyloxy alkyl, monothioacetal, or monothioketal with highly reactive silica surface.

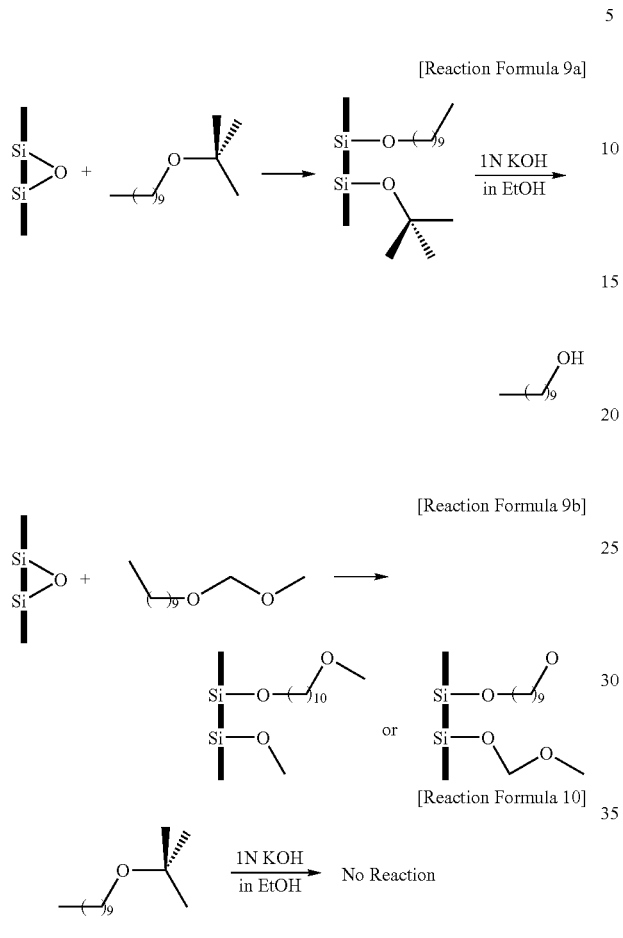

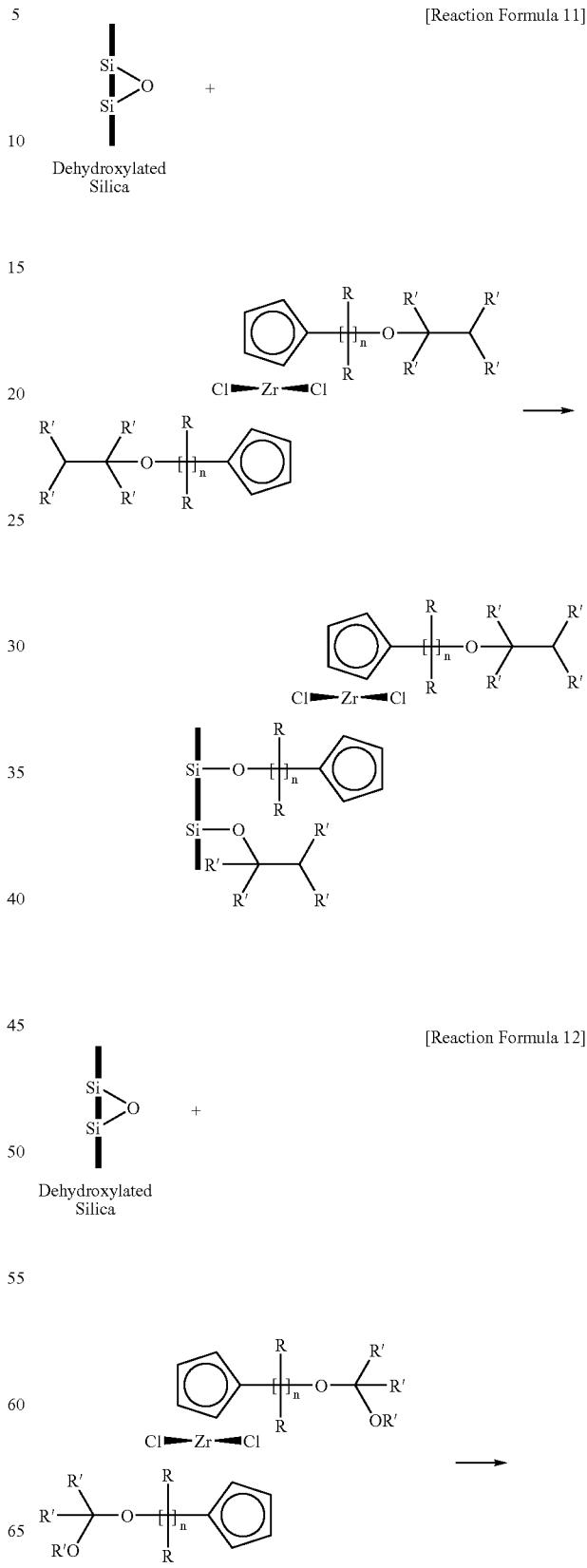

The Reaction Formulae 7a and 7b are one of the major features in this invention and can be explained by the following experiment.

Generally, the C—O bond in the ether, acetal or ketal functional groups is cleaved in the presence of acid, while it is unreactive in basic condition. That is, the tertiarybutyl decyl ether is intact in the ethanol solution of KOH (1N) with or without untreated silica as shown in Reaction Formula 8.

However, the formation of decanol is observed from the tertiarybutyl decyl ether in ethanol solution of KOH (1N) when the silica dehydroxylated above 800° C. is present. This experiment shows that the C—O bond in the tertiarybutyl decyl ether is cleaved upon reaction with the silica dehydroxylated above 800° C. Unlike the C—O bond, the newly formed Si—O bond of the Si—O(CH$_2$)$_9$CH$_3$ in the Reaction Formula 7a is broken easily in the basic solution such as ethanol solution of KOH (1N) to give decanol. Functional groups such as acetal, ketal, tertiary alkoxy alkyl, benzyloxy alkyl, substituted benzyloxy alkyl, monothioacetal, or monothioketal, contain C—O bond which is as reactive as that in tertiarybutyl decyl ether. They show similar reactions to Reaction Formulae 7a and 7b.

The following Reaction Formulae 9~11 show reaction schemes of the metallocene compounds containing functional groups such as acetal, ketal, tertiary alkoxy alkyl,

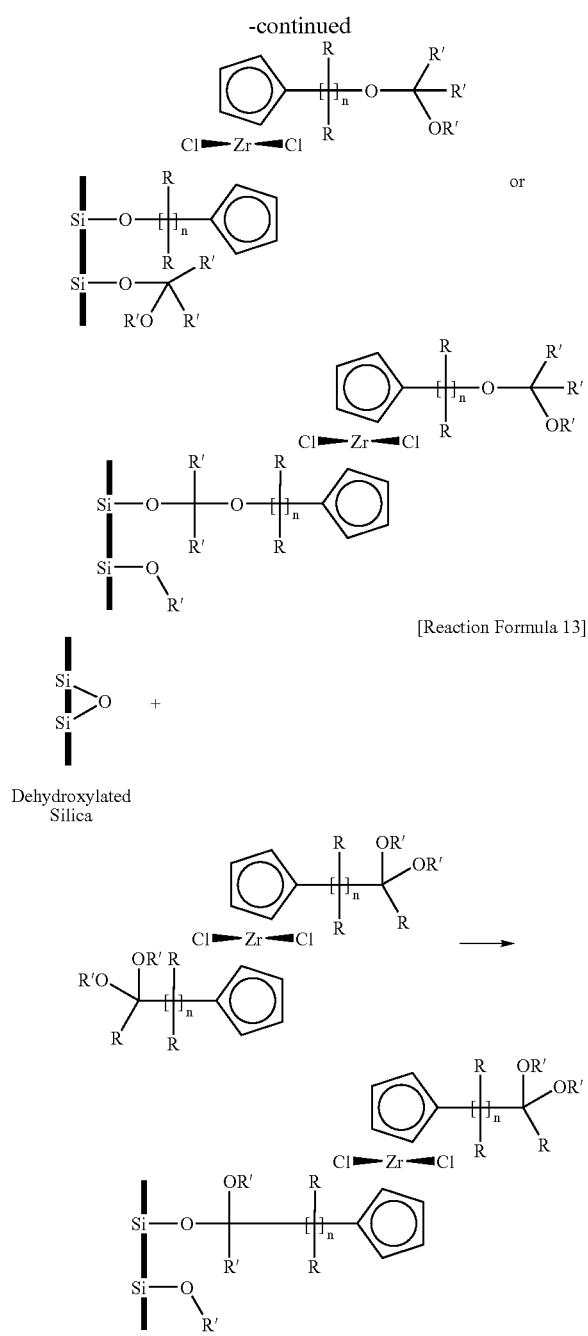

[Reaction Formula 13]

Dehydroxylated Silica wherein each R and R', which can be same or different, are hydrogen radicals, alkyl, cycloalkyl, aryl, alkenyl, alkylaryl, arylalkyl, or arylalkenyl radicals, and two R' can join together to form a ring.

In the preparation of supported metallocene catalyst, the silica which is fully dehydroxylated silica but maintaining the fundamental structures such as surface area, pore volume and pore size is desirable to minimize side reactions during the supporting process. It is also preferable to dry the silica at higher temperature to have more siloxane groups on the silica surface.

Solvents for the impregnation process can be aliphatic hydrocarbon solvents such as hexane, heptane or isobutane, aromatic hydrocarbon solvents such as toluene or benzene, chlorinated hydrocarbon solvents such as dichloromethane, ethers such as diethyl ether or THF (tetrahydrofuran), or other common organic solvents such as acetone or ethylacetate. However, aliphatic hydrocarbon solvents such as hexane, heptane or isobutane are desirable.

The supporting reaction can be performed at the temperature range of −30° C. to 300° C., but preferably from 50° C. to 150° C. When reaction temperature is 50 to 150° C., the prepared supported catalyst shows superior activity. For the olefin polymerization process, the supported catalyst can be prepared as a dried powder phase which is separated by a filtration from the reaction solution followed by a drying step. However, in the slurry process the supported catalyst can be prepared in the same solvent which is used for the olefin polymerization process. Then the catalyst is separated by filtration from the solution (if required, after several washing procedures), and is used directly for the activation and polymerization reactions as a slurry without a drying step.

The supported metallocene catalyst prepared in this method can be used for the olefin polymerization process in combination with co-catalyst of the Chemical Formulae 4, 5, 6, or any mixtures of them. Preferably, the cocatalyst of the Chemical Formula 4 or 5 is used.

Examples of compounds described in the above Chemical Formula 4 include methylaluminoxane, ethylaluminoxane, isobutylaluminoxane, butylaluminoxane, etc.

Examples of metal alkyl compounds described in the above Chemical Formula 5 include trimethylaluminum, triethylaluminum, triisobutylaluminum, tripropylaluminum, tributylaluminum, dimethylchloroaluminum, dimethylisobutylaluminum, ethyldimethylaluminum, diethylchloroaluminum, triisopropylaluminum, tri-s-butylaluminum, tricyclopentylaluminum, tripentylaluminum, triisopentylaluminum, trihexylaluminum, methyldiethylaluminum, tripentylaluminum, tri-p-tolylaluminum, dimethylaluminummethoxide, dimethylaluminumethoxide, etc.

Examples of compounds described in the above Chemical Formula 6 include triethylammoniumtetraphenylborate, tributylammoniumtetraphenylborate, trimethylammoniumtetraphenylborate, tripropylammoniumtetraphenylborate, trimethylammoniumtetrakis(p-tolyl)borate, triethylammoniumtetrakis(o,p-dimethylphenyl)borate, trimethylammoniumtetrakis(o,p-dimethylphenyl)borate, tributylammoniumtetrakis(p-trifluoromethylphenyl)borate, trimethylammoniumtetrakis(p-trifluoromethylphenyl)borate, tributylammoniumtetrapentafluorophenylborate, N,N-diethylaniliniumtetraphenylborate, N,N-dimethylaniliniumtetraphenylborate, N,N-diethylaniliniumtetrakispentafluorophenylborate, diethylammoniumtetrakispentafluorophenylborate, triphenylphosphoniumtetraphenylborate, trimethylphosphoniumtetraphenylborate, triethylammoniumtetraphenylaluminate, tributylammoniumtetraphenylaluminate, trimethylammoniumtetraphenylaluminate, tripropylammoniumtetraphenylaluminate, trimethylammoniumtetrakis(p-tolyl)aluminate, triethylammoniumtetrakis(o,p-dimethylphenyl)aluminate, tributylammoniumtetrakis(p-trifluoromethylphenyl)aluminate, trimethylammoniumtetrakis(p-trifluoromethylphenyl)aluminate, tributylammoniumtetrakispentafluorophenylaluminate, N,N-diethylaniliniumtetraphenylaluminate, N,N-dimethylaniliniumtetraphenylaluminate, N,N-diethylaniliniumtetrakispentafluorophenylaluminate, diethylammoniumtetrakispentafluorophenylaluminate, triphenylphosphoniumtetraphenylaluminate, trimethylphosphoniumtetraphenylaluminate, triethylammoniumtetraphenylborate, tributylammoniumtetraphenylborate, trimethylammoniumtetraphenylborate, tripropylammoniumtetraphenylborate, trimethylammoniumtetrakis(p-tolyl)borate, tripropylammoniumtetrakis(p-tolyl)borate, triethylammoniumtetrakis(o,p-dimethylphenyl)borate, trimethylammoniumtetrakis(o,p-dimethylphenyl)borate, tributylammoniumtetrakis(p-trifluoromethylphenyl)borate, trimethylammoniumtetrakis(p-trifluoromethylphenyl)borate, tributylammoniumtetrakispentafluorophenylborate, N,N-diethylaniliniumtetraphenylborate, N,N-diethylaniliniumtetraphenylborate, N,N-diethylaniliniumtetrakispentafluorophenylborate, diethylammoniumtetrkispentafluorohenylborate, triphenylphsphoniumtetraphenylborate, triphenylcarboniumtetraphenylborate, triphenylcarboniumtetraphenylaluminate, triphenylcarboniumtetrakis(p-trifluoromethylphenyl)borate, triphenylcarboniumtetrakispentafluorophenylborate, etc.

In the olefin polymerization process utilizing the supported metallocene catalyst with the co-catalyst described above, solvent can be selected from aliphatic hydrocarbon solvents containing 3 to 12 carbons such as propane, butane, isobutane, pentane, hexane, heptane, nonane, decane, or isomers of them, aromatic hydrocarbon solvents such as toluene or benzene, chlorinated hydrocarbon solvents such as dichloromethane or chlorobenzene, or any mixtures of them.

It is also possible to perform the olefin polymerization process in a gas phase or a bulk phase with the metallocene catalyst and the co-catalyst without employing any solvent.

Examples of olefin based monomer, which is capable of polymerization by using the metallocene catalyst or supported metallocene catalyst with the co-catalyst described above include ethylene, α-olefin, cyclic olefin, etc., or olefinic monomers having more than two double bonds such as diene monomers, triene monomers, or polyene monomers. Examples of the monomers described above include ethylene, propylene, 1-butene, 1-pentene, 2-butene, 2-pentene, 4-methyl-1-pentene, 1-hexene, 1-heptene, 1-octene, 1-nonene, 1-decene, 1-undecene, 1-dodecene, 1-tetradecene, 1-hexandecene, 1-icocene, norbornene, norbornadiene, ethylidenenorbornene, vinylnorbornene, dicyclopentadiene, 1,4-butadiene, 1,5-pentadiene, 1,6-hexadiene, styrene, α-methylstyrene, divinylbenzene, or 3-chloromethylstyrene, etc. Co-polymerization can be accomplished by employing more than one of these monomers.

Polymerization is performed at the temperature range of −25° C. to 500° C. and the pressures ranging from 0.001 to 3000 atm. It is preferable to add co-catalyst in an amount that is 1 to 30,000 times the metallocene compound mole content.

In the present invention, contact order and input order of catalyst, co-catalyst, solvent, and monomer are not particularly restricted. That is, polymerization is done by putting the above described supported catalyst and co-catalyst into suspension solvents simultaneously, or main polymerization can be performed after either the activation reaction or pre-polymerization.

The main polymerization can be carried out in a suitable suspension solution by introducing monomers. It may also be done in a gas phase or in a bulk phase without diluent. Pre-polymerized catalyst is prepared from the supported catalyst mixed with the co-catalyst under the suitable olefin polymerization conditions of temperature and pressure. It is then separated either by a filtration or decantation. Activated catalyst can be obtained by the same method of pre-polymerization reaction but without olefin. Treatment of the supported catalyst with organic aluminum compound before the polymerization process can reduce the amount of methylaluminoxane required.

Although the present invention is illustrated by the following practical exercises in detail, the range of the present invention is not limited by these practical exercises.

EXAMPLES

Organic reagents and solvents for the catalyst synthesis and polymerization process were purchased from Aldrich or Merck and then refined by standard methods. High purity ethylene gas, Applied Gas Technology, was polymerized after passing through a moisture and oxygen scavenging filter. Reproducibility was maintained by performing all stages of catalyst synthesis, impregnation and polymerization under inert gas atmosphere.

The catalysts were analyzed by a Nuclear Magnetic Resonance (NMR) spectroscopy employing a 300 MHz Bruker instrument.

Bulk density was obtained with Apparent Density Tester 1132 made by Prüftechnic according to the ISO R 60 and DIN 53466.

Molecular weight and the distribution of molecular weight were obtained using gel permeation chromatography, Waters Model 150CV+ GPC. The data were obtained at 140° C. with trichlorobenzene as a solvent and were analyzed using polystyrene analyzing curve.

Microscope image was obtained on a Nikon OPTIPHOT2-POL.

Example 1

(Synthesis of [methoxymethyl-O—$(CH_2)_6$—$C_5H_4]_2$ $ZrCl_2$)

6-Chlorohexyl-1-methyl-1-methoxyethyl ether was synthesized from 6-chlorohexanol and 2-methoxypropene by the literature method (Klug, A. F.; Untch, K. G.; Fried, J. H. *J. Am. Chem. Soc.* 94, 7827, (1972)). To this, 1 equivalent of NaCp (2.0 M in THF) was added and stirred overnight. Water was added to this solution and the organic layer was extracted and dried with $MgSO_4$. The solvent was removed and methoxymethyl-O—$(CH_2)_6$—$C_5H_5$ was obtained by a vacuum distillation (around 80° C./0.1 mmHg; Yield was 56% based on 6-chlorohexanol).

This compound, 1.349 g, is dissolved in 5 mL of THF and cooled down to −40° C. To this solution 1 equivalent of "BuLi (in hexane) was added and the solution was stirred for 3 hours with a slow warming to room temperature. This solution was then added to a flask containing 0.5 equivalent of $ZrCl_4(THF)_2$ at 55° C. and was agitated for 40 hours. The solvent was removed by a distillation and 30 mL of hexane was added. Filtration at 55° C. followed by a removal of hexane gave 1.711 g of the product (Yield: 92%). This product was used for the preparation of supported catalyst without a further purification step.

Spectroscopic analysis of the product by the NMR method is as follows:

$^1$H NMR (δ, 300 MHz, $CDCl_3$): 6.28 (t, J=2.7 Hz, 2 H), 6.19 (t, J=2.7 Hz, 2 H), 4.61 (s, 2 H), 3.50 (t, J=6.5 Hz, 2 H), 3.35 (s, 3 H), 2.63 (t, J=8 Hz, 2 H), and 1.6-1.3 (m, 8 H);

$^{13}$C NMR (δ, $CDCl_3$): 135.00, 116.69, 112.17, 96.38, 67.72, 55.09, 30.58, 30.09, 29.63, 29.09, and 25.95.

Example 2

(Synthesis of [1-methyl-1-methoxyethyl-O—(CH$_2$)$_6$—C$_5$H$_4$]$_2$ZrCl$_2$)

1-methyl-1-methoxyethyl-O—(CH$_2$)$_6$—Cl was prepared from 6-cholrohexanol by the literature method (J. Am. Chem. Soc. 7827, (1972)). 1-methyl-1-methoxyethyl-O—(CH$_2$)$_6$—C$_5$H$_5$ was obtained from the reaction with NaCp by the method described above (Yield: 44%).

The product was obtained by the same method described above except for that zirconation was accomplished at room temperature. This compound is relatively stable in a solution state but is unstable in the absence of solvent.

$^1$H NMR (δ, 270 MHz, CDCl$_3$): 6.28 (t, J=3.0 Hz, 2 H), 6.19 (t, J=3.0 Hz, 2 H), 3.37 (t, J=6.8 Hz, 2H), 3.18 (s, 3 H), 2.63 (t, J=8 Hz, 2 H), 1.6-1.3 M, 8 H), and 1.33 (6 H).

Example 3

(Synthesis of [tetrahydropyranyl-O—(CH$_2$)$_6$—C$_5$H$_4$]$_2$ZrCl$_2$)

Tetrahydropyranyl-O—(CH$_2$)$_6$—Cl was prepared from 6-cholrohexanol by the literature method (Synthesis 618, (1979)). Tetrahydropyranyl-O—(CH$_2$)$_6$—C$_5$H$_5$ was obtained from the reaction with NaCp by the method described above (Yield: 58%).

The product was obtained by the same method described above (Yield: 58%).

$^1$H NMR (δ, 300 MHz, CDCl$_3$): 6.28 (t, J=2.6 Hz, 2 H), 6.19 (t, J=2.6 Hz, 2 H), 4.6-4.5 (m, 1 H), 3.9-3.8 (m, 1 H), 3.71 (dt, J=9.6 Hz, 1 H), 3.5-3.4 (m, 1 H), 3.36 (dt, 9.6, 6.8 Hz, 1 H), 2.62 (t, J=8 Hz, 2 H), and 1.9-1.2 (m,14 H);

$^{13}$C NMR (δ, CDCl$_3$): 135.01, 116.66, 112.23, 98.86, 67.52, 62.36, 30.77, 30.60, 30.10, 29.64, 29.12, 25.98, 25.48, and 19.70.

Example 4

(Synthesis of [1-ethoxyethyl-O—(CH$_2$)$_6$—C$_5$H$_4$]$_2$ZrCl$_2$)

1-ethoxyethyl-O—(CH$_2$)$_6$—Cl was prepared from 6-cholrohexanol by the literature method (Chem. Ind. (London) 1710, (1964)) and 1-ethoxyethyl-O—(CH$_2$)$_6$—C$_5$H$_5$ was obtained from the reaction with NaCp by the method described above (Yield: 69%).

The product was obtained by the same method described above (Yield: 80%)

$^1$H NMR (δ, 300 MHz, CDCl$_3$): 6.29 (t, J=2.6 Hz, 2 H), 6.20 (t, J=2.6 Hz, 2 H), 4.67 (q, J=5.3 Hz, 1 H), 3.7-3.3 (m, 4 H), 2.63 (t, J=8 Hz, 2 H), 1.7-1.2 (m, 8 H), 1.29 (d, J=5.3 Hz, 3 H), and 1.20 (t, J=7.1 Hz, 3 H);

$^{13}$C NMR (δ, CDCl$_3$): 134.93, 116.62, 112.14, 99.47, 65.10, 60.63, 30.52, 30.03, 29.72, 29.06, 25.93, 19.83, and 15.27.

Example 5

(Synthesis of [t-butyl-O—(CH$_2$)$_6$—C$_5$H$_4$]$_2$ZrCl$_2$)

Tertiary-butyl-O—(CH$_2$)$_6$—Cl was prepared from 6-cholrohexanol by the literature method (Tetrahedron Lett. 2951, (1988)) and t-butyl-O—(CH$_2$)$_6$—C$_5$H$_5$ was obtained from the reaction with NaCp by the same method described above (Yield: 60%, b.p. around 80° C. at 0.1 mmHg).

The product was obtained by the same method described above (Yield: 92%).

$^1$H NMR (δ, 300 MHz, CDCl$_3$): 6.28 (t, J=2.6 Hz, 2 H), 6.19 (t, J=2.6 Hz, 2 H), 3.31 (t, J=6.6 Hz, 2 H), 2.62 (t, J=8 Hz), 1.7-1.3 (m, 8 H), and 1.17 (s, 9 H);

$^{13}$C NMR (δ, CDCl$_3$): 135.09, 116.66, 112.28, 72.42, 61.52, 30.66, 30.61, 30.14, 29.18, 27.58, and 26.00.

Example 6

(Preparation of the Supported Catalyst)

Silica support, Grace Davison (XPO 2412), was dehydroxlated at 800° C. under vacuum.

To each glass reactor charged with 1.0 g of silica and 20 mL of hexane, were added 10 mL of hexane solution containing 100 mg of the catalyst prepared in the above Examples 1~5. The solution was stirred for 3 hours at 85° C. and hexane was removed by a decantation. Remained hexane was removed under reduced pressure to give supported catalyst.

Example 7

(Polymerization)

In a dry box 100 mg of the supported catalyst was weighed and transferred to a glass reactor. The glass reactor was sealed, removed from the dry box and filled with 50 mL of hexane and MAO solution dissolved in hexane or heptane solution (1.0 mmole of Al). The solution was stirred for 30 minutes at 40° C. and then pre-polymerized with 30 psig ethylene atmosphere for 30 minutes at room temperature.

The pre-polymerized catalyst prepared above and 660 mL of hexane solution containing 1.0 mmole of triethylaluminum were transferred to a Büchi reactor under an inert gas atmosphere. Polymerization was performed at 80° C. for 60 minutes under 130 psig atmosphere of ethylene. Upon the completion of the polymerization, ethylene was removed by ventilation. The obtained polymer was filtered and dried at 80° C. in an oven Table 1 shows activity, bulk density, molecular weight, and distribution of molecular weight for the catalysts prepared above.

Bulk density of the polymer was 0.36~0.39 g/mL and no fouling in the reactor was observed.

Figure 2:
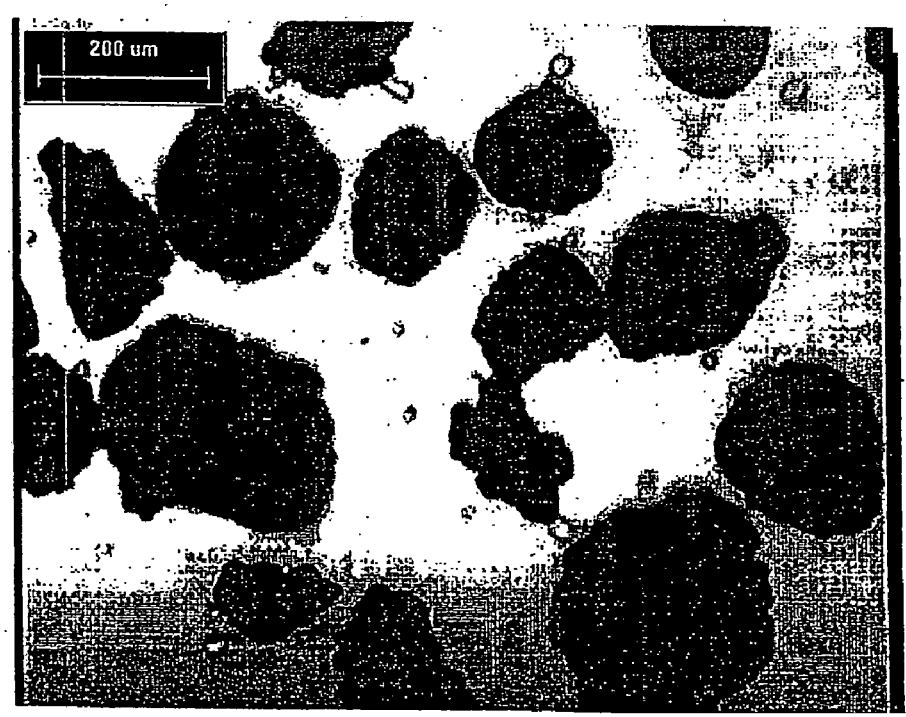
FIG. 2 is an optical microscope photograph of the polymer morphology (40 times magnified). The polymer here is prepared from the supported catalyst which is prepared by supporting catalyst of example 5 onto a silica surface.

FIG. 1 shows the morphology of the supported catalyst and FIG. 2 shows the morphology of the polymer prepared from the supported catalyst of the [t-butyl-O—(CH$_2$)$_6$—C$_5$H$_4$]$_2$ZrCl$_2$. FIGS. 1 and 2 show the similarities of the morphology of the polymer and that of the catalyst. It was also observed that the morphology of polymers obtained from catalysts shown in Table 1 were similar to FIG. 2.

Comparative Example 1

Preparation of a supported catalyst, pre-polymerization, and main polymerization were carried out according to example 6 and 7 using bis(octylcycloentadienyl)zirconium dichloride which has no functional group capable of reaction with silica and was claimed in U.S. Pat. No. 5,324,800.

Figure 3:
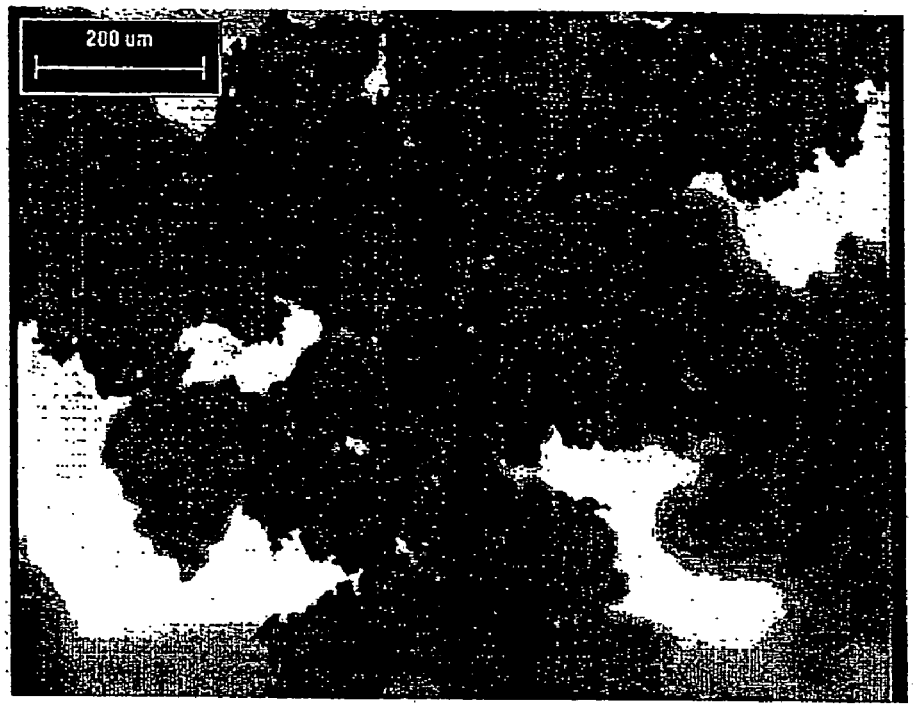
FIG. 3 is an optical microscope photograph of the polymer morphology (40 times magnified). The polymer here is prepared from the supported catalyst which is prepared by supporting catalyst of comparative example 1 onto a silica surface.

The yield was 51 g and a severe fouling was observed during the preliminary and main polymerization. The morphology was poor and the bulk density was 0.04 g/mL (Table 1). FIG. 3 shows its irregular morphology.

Comparative Example 2

The catalyst compound [2-ethoxyethyl-O—(CH$_2$)$_6$—C$_5$H$_4$]$_2$ZrCl$_2$ which is similar to a catalyst shown in examples of U.S. Pat. Nos. 5,814,574 and 5,767,209 was prepared by the literature method (*J. Organomet. Chem. Vol.* 552, 313, (1998)) published by this inventor. This compound has a primary alkyl chain which shows relatively high Lewis basicity, and has 4 oxygen atoms. The presence of 4 oxygen atoms is good for a binding to an inorganic support by a Lewis acid-base interaction but the C—O bond is difficult to be cleaved. This catalyst is supported by the same method described in Example 6 and then preliminary and main polymerization were performed.

Figure 4:
FIG. 4 is an optical microscope photograph of the polymer morphology (40 times magnified). The polymer here is prepared from the supported catalyst which is prepared by supporting catalyst of comparative example 2 onto a slilca surface.

The polymer obtained was only 7 g and severe fouling was observed. The morphology was very irregular and the bulk density was only 0.08 g/mL. FIG. 4 shows its poor morphology.

Comparative Example 3

Polymerization was performed with [2-ethoxyethyl-O—$(CH_2)_6$—$C_5H_4]_2ZrCl_2$ which is bound to and supported on a $MgCl_2$. $MgCl_2$ was described as a suitable support in the U.S. Pat. No. 5,814,574 on row 4, line 57

26.5 mg of [2-ethoxyethyl-O—$(CH_2)_6$—$C_5H_4]_2ZrCl_2$ was mixed with 600 mg of the ball-milled anhydrous magnesium dichloride, and the mixture was agitated for 2 hours in 30 mL of hexane. Hexane was removed by a decantation and the supported catalyst was washed again. Remained hexane was removed under a reduced pressure. 100 mg of the supported catalyst was transferred to a glass reactor and 250 mL of hexane and 1.6 mL of MAO solution were added to this reactor. The solution was stirred for 5 minutes at 80° C. Polymerization was performed at 40 psig of ethylene atmosphere for an hour. Reactor fouling was observed and irregular morphology was observed. 7.4 g of polyethylene was obtained with the bulk density of 0.10 g/mL.

method (Tetrahedron Lett. 2951 (1988)). The suspension was stirred for 2 hours at 90° C. and unreacted tertiary butyl decyl ether was removed under a reduced pressure. For a complete removal of unreacted tertiary butyl decyl ether, the powder was dried at 150° C. for a day under the reduced pressure of 1 torr. 0.5 g of this powder was added to a 5 mL of ethanol solution of KOH (1N) and stirred for 5 hours at room temperature. The resulting solution was transferred to a separatory funnel containing diethyl ether and water, and diethyl ether layer was separated. This organic layer was dried with $MgSO_4$, and ether was removed to give 15 mg of organic compound. $^1H$ NMR analysis showed that most of the compound is decanol.

To see if the C—O bond of the tertiary butyl decyl ether is cleaved under the above basic condition i.e., ethanol solution of KOH (1N) or ethanol solution of KOH (1N) containing silica, the following experiment was performed. When tertiary butyl decyl ether was reacted with the 5 mL of ethanol solution of KOH (1N) at room temperature for a day, TLC analysis showed the presence of the tertiary butyl decyl ether without any change. There is no change in the tertiary butyl decyl ether at 80° C. for a day of reflux in the ethanol solution of KOH. Reflux of the solution with 0.5 g of silica for a day at 80° C. yielded unreacted tertiary butyl decyl ether on the TLC analysis.

This experiment showed the C—O bond is cleaved only when the tertiary butyl decyl ether is treated with silica dehydroxylated at 800° C.

The metallocene compounds in this invention are supported on the inorganic support strongly due to the strong

TABLE 1

| Classification | Compound | Activity (g) | Bulk density (g/mL) | Mw ($\times 10^{-3}$) | Mw/Mn |
|---|---|---|---|---|---|
| Example 1 | [methoxymethyl-O—$(CH_2)_6$—$C_5H_4]_2ZrCl_2$ | 53 | 0.39 | 241 | 2.5 |
| Example 2 | [1-methyl-1-methoxyethyl-O—$(CH_2)_6$—$C_5H_4]_2ZrCl_2$ | 70 | 0.36 | 248 | 2.5 |
| Example 3 | [tetrahydropyranyl-O—$(CH_2)_6$—$C_5H_4]_2ZrCl_2$ | 80 | 0.38 | 240 | 2.4 |
| Example 4 | [1-ethoxyethyl-O—$(CH_2)_6$—$C_5H_4]_2ZrCl_2$ | 79 | 0.37 | 234 | 2.5 |
| Example 5 | [t-butyl-O—$(CH_2)_6$—$C_5H_4]_2ZrCl_2$ | 101 | 0.36 | 226 | 2.6 |
| Comparative Example 1 | [$CH_3$—$(CH_2)_7$—$C_5H_4]_2ZrCl_2$ | 51 | 0.04 | 290 | 2.5 |
| Comparative Example 2 | [2-ethoxyethyl-O—$(CH_2)_6$—$C_5H_4]_2ZrCl_2$ | 7 | 0.08 | 377 | 2.6 |

As can be seen from the above Table 1, the supported metallocene catalysts prepared from the metallocene compounds of the present invention comprising a functional group such as 1-methyl-1-methoxyethyl, tetrahydropyranyl, or 1-ethoxylethyl and t-butyl showed superior activity for olefin polymerization, compared to those comprising other functional groups.

Example 8

(Experiment to Test the Formation of New Chemical Bond on the Surface Upon the Breakage of the C—O Bond)

The following model experiment was done to show the formation of new chemical bond on the surface upon the breakage of the C—O bond, which is one of the major characteristics of this invention.

The dehydroxylated silica prepared in Example 5 was treated with tertiary butyl decyl ether (t-Butyl-O—$(CH_2)_9$—$CH_3$) which was prepared from decanol by the literature chemical bond between the ligand of the metallocene compound with the silica surface, which leads to a minimized leaching of the catalyst during the activation process.

Therefore, in the olefin polymerization process the supported catalyst in this invention proceeds without fouling in the reactor of a slurry or a gas phase process, and the morphology and bulk density of the polymer produced are better defined than that produced by the conventional method.

Examples 9 and 10 and Comparative Example 4

[Effect of Carbon Distance Between Cp and Functional Group on the Activity of Catalyst]

This is to show the effects of carbon distance between Cp and functional group on the activity of a supported catalyst.

Compounds of the following structure with carbon lengths (n) of 2, 4, 6 and 8 were respectively prepared:

[Structure diagram: Me₂C—O—(CH₂)ₙ—(cyclopentadienyl)₂ZrCl₂—(CH₂)ₙ—O—CMe₃]

Example 9

(Synthesis of [t-butyl-O—(CH$_2$)$_4$—C$_5$H$_4$]$_2$ZrCl$_2$)

The tile compound was prepared by the same method as in Example 5, except that 4-chlorobutanol was used.

$^1$H NMR (400 MHz, CDCl$_3$): δ6.29 (t, 2 H), 6.21 (t, 2 H), 3.34 (t, 2 H), 2.65 (t, 2 H), 1.59 (m, 4 H), 1.17 (s, 9 H);

$^{13}$C NMR (400 MHz, CDCl$_3$): δ135.6, 117.6, 113.1, 73.3, 62.0, 31.0, 30.7, 28.3.

Example 10

(Synthesis of [t-butyl-O—(CH$_2$)$_8$—C$_5$H$_4$]$_2$ZrCl$_2$)

The tile compound was prepared by the same method as in Example 5, except that 8-chlorooctanol was used.

$^1$H NMR (400 MHz, CDCl$_3$): δ6.29 (br s, 2 H), 6.20 (br s, 2 H), 3.31 (m, 2 H), 2.61 (m, 2 H), 1.52 (br m, 4 H), 1.29 (br s, 8 H), 1.18 (s, 9 H);

$^{13}$C NMR (400 MHz, CDCl$_3$): δ135.8, 117.4, 113.1, 73.1, 62.4, 31.4, 30.9, 30.2, 30.1, 30.0, 28.3, 27.0.

Comparative Example 4

(Synthesis of [t-butyl-O—(CH$_2$)$_2$—C$_5$H$_4$]$_2$ZrCl$_2$)

The tile compound was prepared by the same method as in Example 5, except that 2-chloroethanol was used.

$^1$H NMR (400 MHz, CDCl$_3$): δ6.30 (s, 4H), 3.42 (t, 2H), 2.83 (t, 2H), 1.16 (s, 9H);

$^{13}$C NMR (400 MHz, CDCl$_3$): δ132.4, 118.2, 113.5, 73.7, 62.4, 32.4, 28.3.

Example 11

(Preparation of the Supported Catalyst)

Supported catalysts (n=2, 4, 6, 8) were prepared by the same method as in Example 6 using the catalysts from the above Example 5, Example 9, Example 10 and Comparative Example 4, respectively. In this preparation, molar ratios of each zirconium to the silica (1 g) are all equivalent to 0.165 mmol.

Polymerization

Hexane (500 mL) and an appropriate amount of MAO solution were fed into a 1 L glass reactor. And then, each zirconium solution (Al/Zr=500) was injected into the reactor, and the mixture was heated up to 80° C. for 5 min. Polymerization was performed by continuous feed of ethylene at 4 bar for 30 min. The reaction was stopped by addition of MeOH. Concentrated HCl was added, and the suspension was stirred overnight. After filtration, the polymer was dried under vacuum at 80° C. The yield, activity, molecular weights and molecular weight distributions (M$_w$/M$_n$) of the polymers were measured, and shown in Table 2.

TABLE 2

| Example | Carbon Length (n) | Yield (g) | Activity[1] | Mw | Mw/Mn |
|---|---|---|---|---|---|
| Comparative Example 4 | C2 | Trace | — | — | — |
| Example 9 | C4 | 2.50 | 100 | 133,780 | 2.60 |
| Example 5 | C6 | 5.80 | 232 | 147,390 | 2.61 |
| Example 10 | C8 | 2.74 | 110 | 92,830 | 3.02 |

[1]g PE/g Cat · hr

As can be seen from the above Table 2, there is optimum distance between Cp and a functional group to produce an active supported catalyst. When carbon length (n) is 6, produced supported catalyst (Example 5) is the most active for ethylene polymerization. In cases of carbon length less than 4 or more than 8, their activities will be hampered by possible catalyst deactivation reactions. Therefore, it can be confirmed that 4 to 8 carbon lengths of the metallocene compounds are the most preferred structures.

Although preferred embodiments of the present invention have been described in detail hereinabove, it should be clearly understood that many variations and/or modifications of the basic inventive concepts herein taught which may appear to those skilled in the present art will still fall within the spirit and scope of the present invention, as defined in the appended claims.

What is claimed is:

1. A metallocene compound represented by the following Chemical Formula 1:

[Chemical Formula 1]

$$Q_2M \begin{matrix} Cp-(CH_2)a-O-A' \\ Cp-(CH_2)a-O-A' \end{matrix}$$

wherein M is a transition metal of Group 4;

Cp denotes a cyclopentadienyl ring unsubstituted or substituted by hydrogen, alkyl, cycloalkyl, aryl, alkenyl, alkylaryl, arylalkyl or arylalkenyl radicals;

Qs, which are the same or different, are halogen radicals, alkyl, alkenyl, aryl, alkylaryl, or arylakyl radicals having 1 to 20 carbon atoms, or alkylidene radicals having 1 to 20 carbon atoms;

A' is methoxymethyl, t-butoxymethyl, tetrahydropyranyl, tetrahydrofuranyl, 1-ethoxyethyl, 1-methyl-1-methoxyethyl, or t-butyl; and a is an integer of 4 to 8.

2. The metallocene compound according to claim 1, wherein A' is t-butyl.

3. The metallocene compound according to claim 1, wherein a is 6.

4. A metallocene compound represented by the following Chemical Formula 7 or 8:

[Chemical Formula 7]

$(C_5R^1{}_m)_pB_s(C_5R^1{}_m)MQ_{3-p}$

[Chemical Formula 8]

$$B_x \begin{matrix} (C_5R^1{}_n) \\ JR^2{}_{z-y} \end{matrix} M \begin{matrix} L_w \\ Q \\ Q \end{matrix}$$

(wherein M is a transition metal of Group 4 (IVA in the previous IUPAC form);

$(C_5R^1_m)$ and $(C_5R^1_n)$ are a cyclopentadienyl, a substituted cyclopentadienyl ligand, or a substituted cyclopentadienyl ligand in which two adjacent carbon atoms of a $C_5$ are joined together to form one or more $C_4$-$C_{16}$ rings by a hydrocarbyl radical, in which each $R^1$, which is the same as or different from the other $R^1$, is a hydrogen radical, or an alkyl, cycloalkyl, aryl, alkenyl, alkylaryl, arylalkyl, or arylalkenyl radical having from 1 to 40 carbon atoms, or a metalloid of Group 14 (IVB in the previous IUPAC form) substituted by hydrocarbyl radicals;

E is an alkylene carbon chain, arylene carbon chain, alkenylene carbon chain, dialkyl germaniun, dialkyl silicon, alkyl phosphine, or alkyl amine radical substituting on and bridging two cyclopentadienyl ligands, or a cyclopentadienyl ligand and $JR^2_{z-y}$ ligands by a covalent bond;

$R^2$ is a hydrogen radical, or an alkyl, aryl, alkenyl, alkylaryl, or arylalkyl radical having from 1 to 40 carbon atoms;

J is an element of Group 15 (VB in the previous IUPAC form) or Group 16 (VIB in the previous IUPAC form);

each Q, which can be the same as or different from the other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1 and p is 0, 1 or 2;

provided the when p is 0, then s is 0; when s is 1, then m is 4; and when s is 0, then m is 5;

z is a valence number of J;

provided that when J is an atom of Group 15 (VB in the previous IUPAC form), then z is 3; and when J is an atom of Group 16 (VIB in the previous IUPAC form), then z is 2;

x is 0 or 1; and provided that when x is 0, then n is 5, y is 1, and w is greater than 0; when x is 1, then n is 4, y is 2, and w is 0);

in which at least one of the hydrogen radical of $R^1$, $R^2$ or E is substituted by a radical selected from the group consisting of the radical represented by the following Chemical Formula 12:

[Chemical Formula 12]

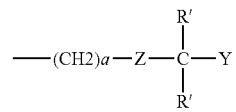

wherein Z is oxygen atom or sulfur atom;

each R', which is the same or different, is an alkyl, cycloalkyl, aryl, alkenyl, alkylaryl, arylalkyl, or arylalkenyl radical having from 1 to 20 carbon atoms and two R' can join together to form a ring;

G is an alkyl, cycloalkyl, aryl, alkenyl, alkylaryl, arylalky, or arylalkenyl radical, alkoxy, aryloxy, alkylthio, arylthio having from 1 to 20 carbon atoms, a phenyl, or a substituted phenyl, and G and R' can join together to form a ring; and a is an integer of 4 to 8, provided that when Z is sulfur atom, then G is alkoxy or aryloxy; and when G is not alkoxy or aryloxy, Z is an oxygen atom.

5. The metallocene compound according to claim 4, wherein in the Chemical Formula 12, G is a hydrogen radical, an alkyl, cycloalky, aryl, alkenyl, alkylaryl, arylalkyl, or arylalkenyl radical having from 1 to 20 carbon atoms, or a substituted or unsubstituted phenyl.

6. The metallocene compound according to claim 4, wherein in the Chemical Formula 12, $CR'_2G$ is t-butyl.

7. The metallocene compound according to claim 4, wherein in the Chemical Formula 12, a is 6.

* * * * *